(12) United States Patent
Schreiber et al.

(10) Patent No.: US 8,981,317 B2
(45) Date of Patent: Mar. 17, 2015

(54) METHOD AND DEVICE FOR DETECTING TUMOROUS LIVING CELL TISSUE

(75) Inventors: Juergen Schreiber, Dresden (DE); Joerg Opitz, Dresden (DE); Carola Gerich, Dresden (DE); Jens Fehre, Hausen (DE); Georg Salomon, Wentorf Bei Hamburg (DE); Ralf Nanke, Neunkirchen am Brand (DE)

(73) Assignees: Fraunhofer-Gesellschaft zur Foerderung der Angewandten Forschung E.V., Munich (DE); Siemens Aktiengesellschaft, Munich (DE)

( * ) Notice: Subject to any disclaimer, the term of this patent is extended or adjusted under 35 U.S.C. 154(b) by 674 days.

(21) Appl. No.: 13/320,610

(22) PCT Filed: May 12, 2010

(86) PCT No.: PCT/DE2010/000559
§ 371 (c)(1),
(2), (4) Date: Feb. 2, 2012

(87) PCT Pub. No.: WO2010/130254
PCT Pub. Date: Nov. 18, 2010

(65) Prior Publication Data
US 2012/0252057 A1    Oct. 4, 2012

(30) Foreign Application Priority Data

May 15, 2009  (EP) .................................. 09006583
Jul. 1, 2009  (DE) ........................ 10 2009 031 775

(51) Int. Cl.
*G01N 21/64*    (2006.01)
*A61B 5/00*    (2006.01)

(52) U.S. Cl.
CPC .......... *G01N 21/6486* (2013.01); *A61B 5/0059* (2013.01); *G01N 21/6408* (2013.01)
USPC .................................. 250/458.1; 250/461.2

(58) Field of Classification Search
CPC .......... G01N 21/6402; G01N 21/6408; G01N 21/6428
USPC ........................................... 250/458.1–461.2
See application file for complete search history.

(56) References Cited

FOREIGN PATENT DOCUMENTS

| DE | 68925586 T2 | 10/1996 |
|---|---|---|
| WO | WO 02/069784 A2 | 9/2002 |
| WO | WO 2009/059072 A2 | 5/2009 |

OTHER PUBLICATIONS

Salomon et al. (2007), "Prostate Cancer Detection by Laser Induced Autofluorescence and Multicomponent Spectroscopy," SPIE Proc. 6734, Int. Conf. on Lasers, Appl. & Tech.: Laser Tech. For Med., 67340H (Aug. 1, 2007).*

(Continued)

*Primary Examiner* — Casey Bryant
(74) *Attorney, Agent, or Firm* — Jacobson Holman, PLLC.

(57) ABSTRACT

The invention relates to a method and to an apparatus for recognizing tumorous living cell tissue. It furthermore relates to a method and to an apparatus for recognizing tumorous cell tissue at collected living cell tissue samples. In the method, electromagnetic radiation is emitted with local definition onto cell tissue by a radiation source and, after deactivation of the radiation source, the decay behavior of the inherent fluorescence intensity of the cell tissue excited by the electromagnetic radiation is detected at the cell tissue in a time resolved and spectrally resolved manner at known sampling rate(s) for at least one wavelength using a detector. The difference autocorrelation function C(t) of the intensity decay behavior is determined using the determined measured intensity values, the fractal dimension $D_F$ for the respective irradiated cell tissue is calculated from this and the value of the fractal dimension $D_F$ is used for a classification with respect to a presence of a tumor in the respective irradiated cell tissue.

15 Claims, 3 Drawing Sheets

(56) References Cited

OTHER PUBLICATIONS

Figure 1:
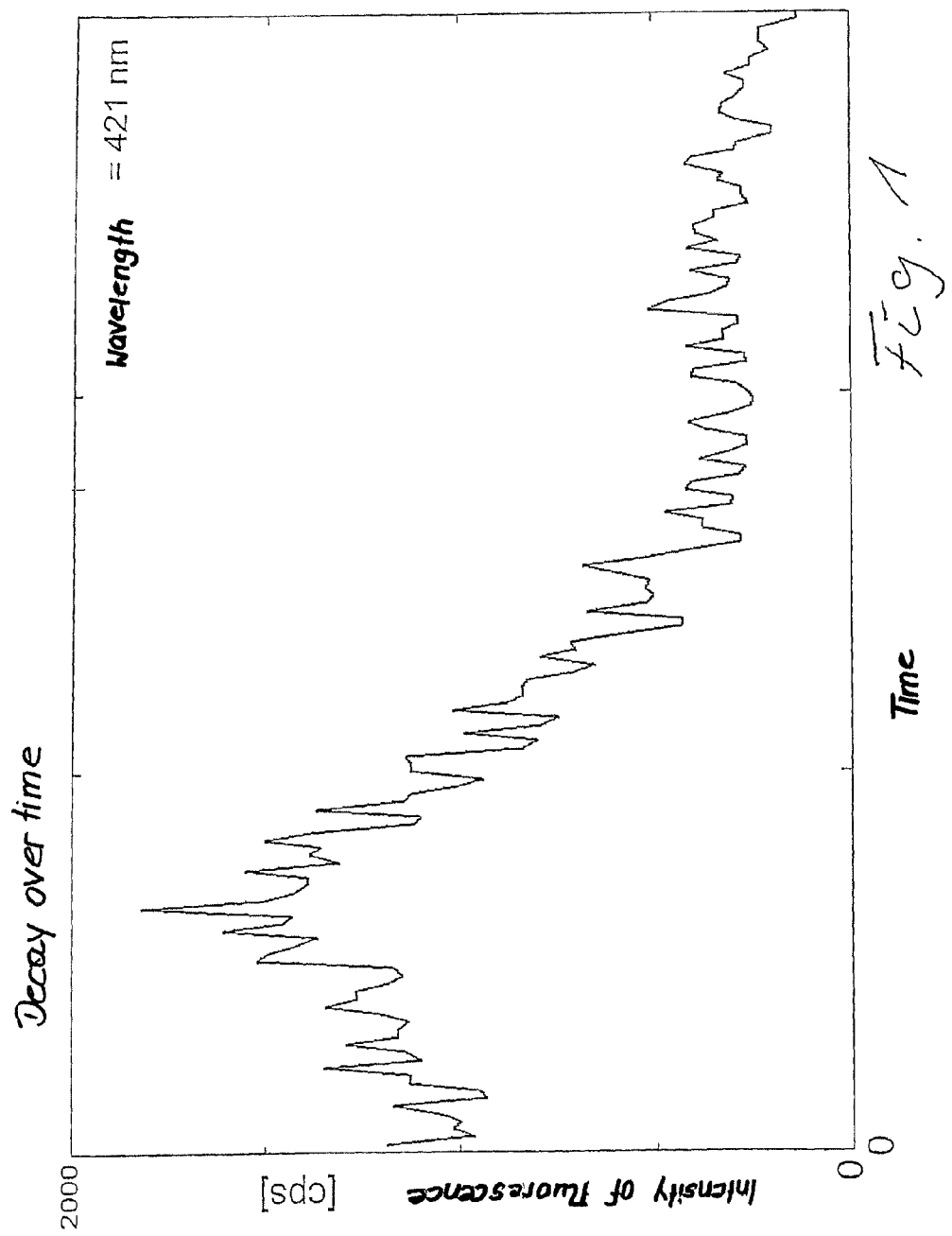

Gerich et al. (2011), "Detection of Cancer-Cells in Prostate Tissue with Time-Resolved Fluorescence Spectroscopy," Optical Interactions with Tissue and Cells XXII, Proc. of SPIE vol. 7897, 78970R1-12.*

Gerich, C.E., et al., Detection of Cancer-Cells in Prostate Tissue with Time-Resolved Fluorescence Spectroscopy, Proc. of SPIE, vol. 7897, Feb. 10, 2011, 7897OR-1 thru12.

M. Weiss et al., "Anomalous protein diffusion in living cells as seen by fluorescence correlation spectroscopy." Biophysical J., vol. 84, No. 6, Jun. 2003, pp. 4043-4052.

N.O. Petersen, "Quantitation of Membrane Receptor Distributions by Image Correlation Spectroscoy: Concept & Application", Biophysical J., vol. 65, No. 4, Sep. 1993, pp. 1135-1146.

A. Benda et al., "TCSPC Upgrade of a Confocal FCS Microscope", Review . of Scientific Instruments, vol. 76, No. 3, Mar. 2005, pp. 033106-1 thru 033106-4.

G. Salomon et al., "Prostate Cancer Detection by Laser Induced Autofluorescence and Multicomponent Spectroscopy", Proceedings of SPIE, vol. 6734, 2007, pp. 2-3.

* cited by examiner

METHOD AND DEVICE FOR DETECTING TUMOROUS LIVING CELL TISSUE

This is a national stage of PCT/DE10/000559 filed May 12, 2010 and published in German, which claims the priority of European number 09006583.0 filed May 15, 2009, and German number 10 2009 031 775.9 filed Jul. 1, 2009, hereby incorporated by reference.

The invention relates to a method and to an apparatus for recognizing tumorous living cell tissue. It furthermore relates to a method and to an apparatus for recognizing tumorous cell tissue at collected living cell tissue samples.

It is common practice with the different types of carcinoma to surgically remove tumorous cell tissue. It is necessary in this respect to completely remove the affected cell tissue so that a progression and spread of the disease can be avoided. It is in particular desirable with prostate cell tissue to maintain a proportion of non-effected cell tissue which is as high as possible to continue to ensure necessary functions (continence, potency). It is therefore necessary to localize tumorous cell tissue in order to be able subsequently surgically to remove affected cell tissue in a more targeted manner.

As a rule, rapid sections are taken directly in a surgical procedure and are pathologically examined in a laboratory. In the examination by a pathologist, the cell tissue sample is deep frozen and sections are prepared from it which are then assessed by the pathologist. A high time expenditure is required for this purpose since not only the sample preparation, but also the documentation and the transportation take up time. Waiting times can also not be avoided. This results in a high stress on the respective patient and blocks an operating room for a longer period.

In addition to the assessment of rapid sections, it is also known to carry out fluorescent cytoscopy for a tumor diagnosis. In this respect, tumorous cell tissue is made photosensitive using suitable chemical substances and on irradiation with light fluorescence is excited at cells prepared in this way. In this respect, the light for excitation has a different color to the fluorescent light. The substances used are, however, highly phototoxic and can cause necrosis at correspondingly treated tissue. This can, however, also be utilized for therapy against carcinogenic tumors. In this respect, however, the knowledge of the position and of the spread of tumorous cell tissue is required.

For the recognition of tumorous cell tissue, so-called 5 ALA induced detection is used in which 5-aminolevulinic acid is injected or methods are used which are known commercially as Hexvix and TOOKAD and in which other photoactive substances are used.

It is disadvantageous in this respect that the substances have to be introduced into the body of a patient which are directly distressing for the respective patient, but also subsequently distressing over a longer time period, since the patient suffers from increased photosensitivity. After the injection of the substances, the examinations cannot be carried out directly afterward since a reaction time has to be waited for which can vary from patient to patient.

In addition, a method is known from DE 689 25 586 T2 for a laser induced fluorescence of tissue, in which one should be able to draw a conclusion on the respective type of cell tissue on a recognition of the respective types of cell tissue by a fluorescence excitation and the detection of specific characteristic wavelengths in the detected wavelength spectrum of the fluorescent light.

It has, however, been found that the inherent fluorescence of the body's own chromophores excitable to be fluorescent in cell tissue which can be tumorous or healthy is not unambiguous with reference to the presence of one wavelength, or optionally also a plurality of wavelengths, which occur(s) in the fluorescent light spectrum since a cooperative behavior of the examined cells cannot be neglected. These different factors and the biomolecular cell structure have a great influence and an association of whether it is healthy or tumorous cell tissue is not possible with sufficient security.

It is therefore the object of the invention to be able to achieve a recognition of tumorous cell tissue in a shorter time and with sufficient security of diagnosis.

In accordance with the invention, this object is achieved by a method having the features of claim 1 or of claim 2. The method can be carried out using an apparatus in accordance with claim 15. Advantageous embodiments and further developments of the invention can be achieved using features designated in the subordinate claims.

The method in accordance with the invention in accordance with claim 1 is carried out on living cell tissue.

In this respect, in accordance with claim 2, the method can also be carried out at a collected living cell tissue sample (in vitro).

Electromagnetic radiation is emitted onto the cell tissue to be examined using a radiation source in a locally defined manner onto the cell tissue sample and after a deactivation of the radiation source at a time $t_0$ the decay behavior of the inherent fluorescence intensity of the cell tissue excited by the electromagnetic radiation is detected in a time-resolved and spectrally resolved manner. The detection of the inherent fluorescence intensity in this respect takes place using one or more known sampling rate(s) and is carried out for at least one wavelength. The sampling rate is preferably held constant in the detection.

The difference autocorrelation function C(t) of the intensity decay behavior is determined in accordance with equations (1) and (2) using the determined measured intensity values while taking account of the respective known sampling rate(s).

$$I(t)=I(t_0)-[I(t_0)-I(t\to\infty)]*[1-R(t-t_0)] \qquad (1)$$

where
t=time, $t_0$=initial time, $$R(t-t_0)=<\Delta I(t)\Delta I(t_0)>_t/<\Delta I^2>_t, \text{ and}$$

$$\Delta I(t)=I(t)-I(t\to\infty) \qquad (2).$$

Here, $I(t\to\infty)$ is the intensity of the excited fluorescent light after infinitely long relaxation which is very small. This relaxation function R(t) results from the correlation function of the fluorescent fluctuations, where $<>_t$ represents the mean time value.

The function C(t)=2[1−R(t)] represents the associated difference correlation function for which the following behavior can be taken into account with cooperative fluorescent procedures:

$$C(t)\sim t^{2H} \qquad (3).$$

The exponent H or the fractal dimension of the stochastic intensity fluctuations $D_F$ which can be calculated therefrom is in this respect a characteristic value for the evaluation.

In this respect, $D_F=2-H$ results and can be used for the examination of healthy and tumorous cell tissue. The exponent H can be determined by linear regresssion.

The value $D_F$ can be used for a classification with respect to the presence of a tumor in the respective irradiated cell tissue.

A comparison can be carried out with a threshold value specific to a tumor for the classification. However, an indication of a probability of a presence of a tumor can also take place in the classification.

While taking account of the equations given, the fractal dimension $D_F$ is calculated for the respective irradiated cell tissue and the value of the determined fractal dimension $D_F$ can then be compared with a threshold value specific to a tumor. When this threshold value is exceeded, the irradiated cell tissue of the cell tissue sample is classified as tumorous. If this threshold value is not reached, the cell tissue is healthy. The threshold value is a numerical value between 1 and 2.

An irradiation, detection and calculation of the fractal dimension $D_F$ can thus be carried out at the examined cell tissue or at the respective cell tissue sample at a plurality of positions in order to localize healthy cell tissue and any tumorous cell tissue present.

On the evaluation of the intensity decay behavior, collective electron transitions in the cell tissue are described via an algebraic time behavior in the invention.

It is preferred to use monochromatic electromagnetic radiation for the inherent fluorescence excitation of the irradiated cell tissue. Electromagnetic radiation in the wavelength range between 200 nm and 650 nm is particularly suitable here. Laser light sources can be used as the radiation source. Electromagnetic radiation with a wavelength of 337 nm has proven favorable for the excitation of the inherent fluorescence.

As already stated, only a selected wavelength from the spectrum of the inherent fluorescence of the cell tissue to be examined can be detected and then taken into account in the invention. Two and more wavelengths can, however, also be taken into account which differ from one another and can then be much larger or smaller with respect to one another.

It is, however, favorable to detect measured intensity values within an interval around a wavelength of the excited inherent fluorescence and to determine the difference autocorrelation function of the intensity decay behavior $C(t)$ of the mean values which have been calculated from the fluorescence intensities simultaneously detected for the different wavelengths within the wavelength interval and to calculate the fractal dimension $D_F$ for the irradiated cell tissue from this.

At least 30 wavelengths from the selected wavelength interval should be considered for the formation of the mean value. The difference of the spacings of the wavelengths from this wavelength interval taken into account in this respect should thus be the same in each case. The detection can thus, for example, be carried out within a wavelength interval of 421 nm±15 nm.

The detection can be carried out using a spectrometer and detection can be performed at a sampling rate≤1000 ps, preferably ≤100 ps, particularly preferably at approximately 50 ps.

The electromagnetic radiation for the excitation of the inherent fluorescence can be directed to the cell tissue via at least one optical fiber and the inherent fluorescent light can be directed to the detector via the same optical fiber(s) after the deactivation of the radiation source. In this respect, a beam splitter can be used with which the electromagnetic radiation used for the detection and emitted as a consequence of the inherent fluorescence of the cell tissue sample can be directed to the detector. It is favorable to carry out the irradiation and the detection inside an optically non-transparent chamber.

Cell tissue samples to be detected should be cooled before and during the detection and in so doing be kept at a constant temperature. In this respect, a temperature of 15° C. should preferably be maintained. A temperature control is favorable to be able to maintain comparable conditions. Cell tissue samples can be cooled on a sample carrier or in the chamber in which the examinations are carried out. Suitable coolants or elements suitable for cooling can be arranged thereat or therein.

Such examinations can be carried out at a plurality of positions at cell tissue or at a cell tissue sample. In this respect, however, in each case the same irradiation should be maintained at the selected positions of the cell tissue or of the cell tissue sample. An area of respectively the same size should thus be irradiated with respectively the same energy. For this purpose, the spacing of one or more optical fibers from the surface of the cell tissue or of the cell tissue sample to be irradiated should be constant. The knowledge of the respective position at the cell tissue or at the cell tissue sample and of the position of the collection has to be detected and to be documented so that they can be traced later for an evaluation and optional, taking into account in a surgical procedure on a patient on whom the examination has been carried out in vivo or from whom the cell tissue sample has been collected, said surgical procedure to be carried out directly subsequently or later.

The examinations at the cell tissue or at a cell tissue sample can be carried out successively or simultaneously at a plurality of positions. In the last-named case, electromagnetic radiation can, for example, be directed at different locations via a plurality of correspondingly arranged optical fibers for exciting the inherent fluorescence on cell tissue or on the cell tissue sample and, after deactivating the radiation source, the intensity $I(t)$ of the electromagnetic radiation emitted from there as a consequence of the inherent fluorescence of the cell tissue can be conducted via optical fibers to a detector.

An examination can be carried out in real time and optionally directly in an operating room using the invention. There is the possibility of distinguishing tumorous cell tissue from healthy cell tissue with a very high possibility. With knowledge of the respective collection location, the invention provides a good basis for a decision on whether and how much cell tissue should be surgically removed.

An apparatus for carrying out the method in accordance with the invention is designed so that living cell tissue or also a collected living cell tissue sample in a mount is acted on in a locally defined manner by electromagnetic radiation emitted by a radiation source and a detector for the time resolved and spectrally resolved detection of the inherent fluorescence intensity of the respective previously irradiated cell tissue is connected to an electronic evaluation unit with which the difference autocorrelation function $C(t)$ can be determined from the determined measured intensity values. The fractal dimension $D_F$ can be calculated using the electronic evaluation unit and this value of the fractal dimension $D_F$ can be compared with a threshold value typical to a tumor.

The apparatus can in this respect be designed so that a part in which at least one detector for the time resolved and spectrally resolved detection of the inherent fluorescence intensity and in which cell tissue can be irradiated is introduced into an organ at which cell tissue should be examined to be able to carry out the examination directly on the living organism.

A time-consuming preparation of the cell tissue to be examined such as is required with a rapid section is dispensed with. The strain on patients on a surgical procedure can thereby be reduced since the examination result is present after a considerably shorter time. It is possible to distinguish very easily between malign and benign cell tissue.

Nor is any injection of additional substances into the bodies of patients required, with the initially named disadvantages.

The invention should be further explained by way of example in the following.

Figure 2:
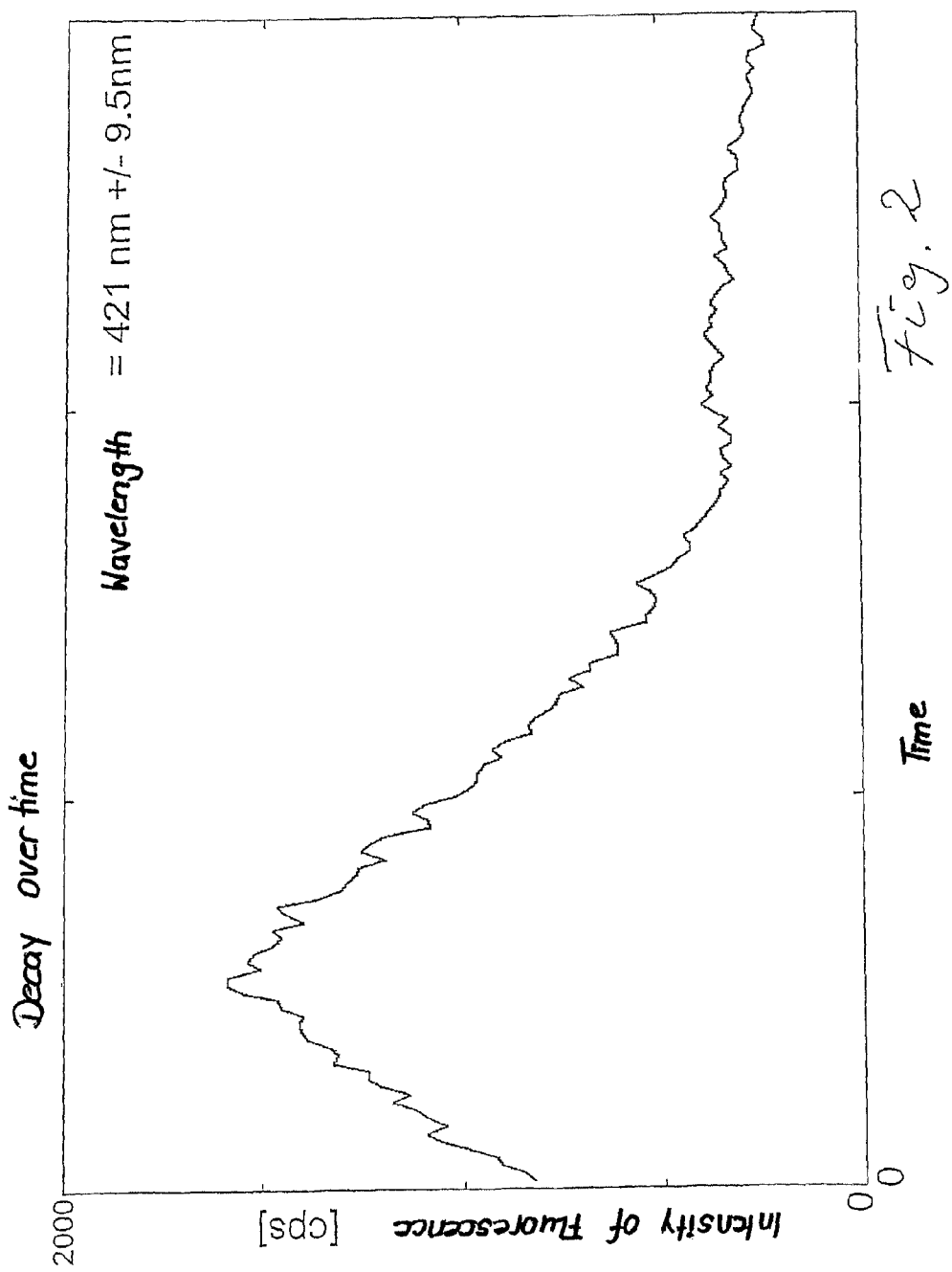
Figure 3:
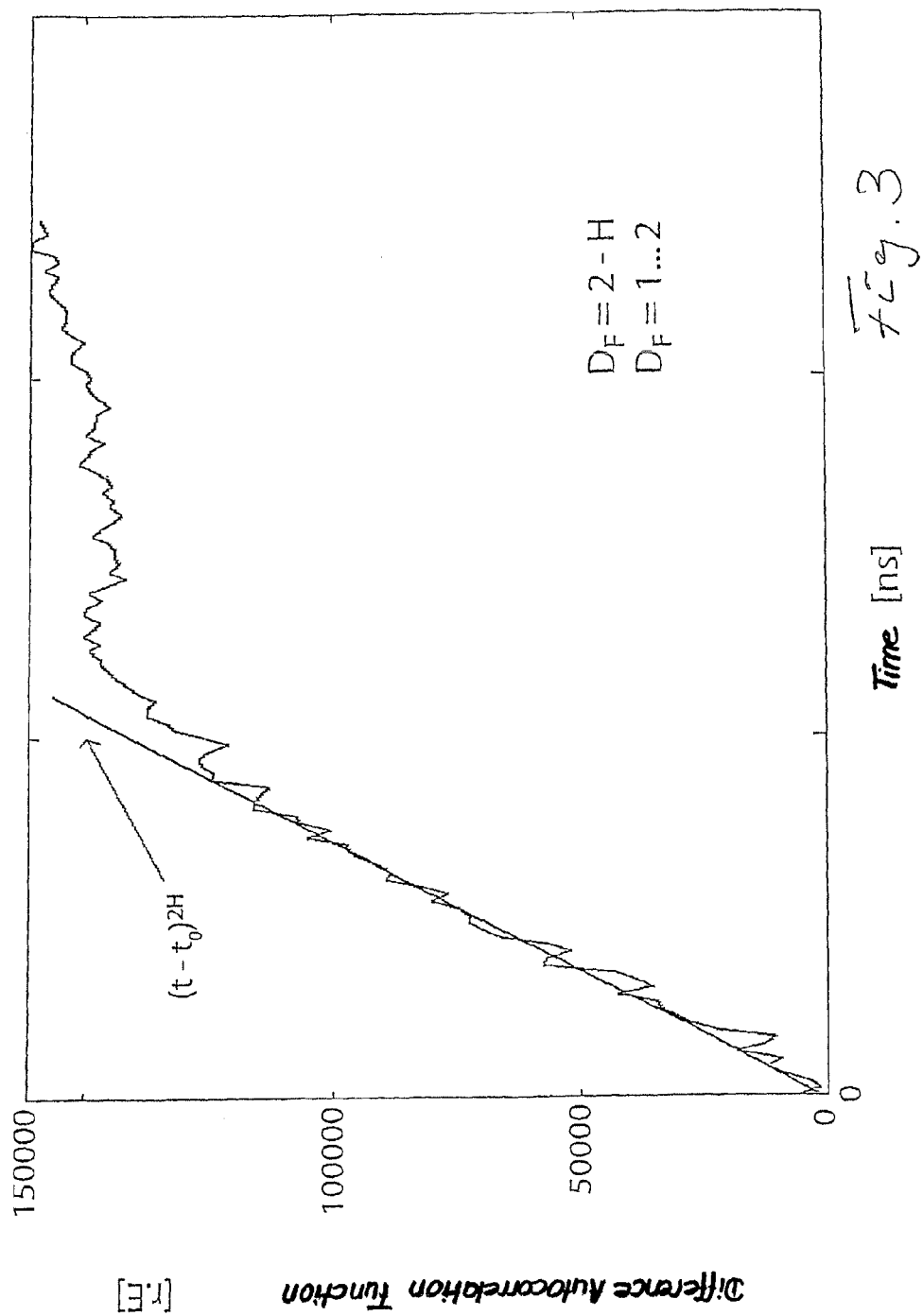

There are shown:

FIG. 1 a diagram of the intensity decay behavior detected with time resolution at a constant wavelength of 421 nm;

FIG. 2 a diagram of the intensity decay behavior which was detected with time resolution and which has been prepared with the mean value of a plurality of wavelengths within a wavelength interval around the wavelength 421; and FIG. 3 the curve of the difference autocorrelation function over time on the decay of the intensity.

Prostate cell tissue was collected from patients in the form of swages for the examinations. The cell tissue samples obtained in this manner were placed into a groove which represented a mount for the cell tissue samples and electromagnetic radiation was directed via an optical fiber onto specific predefined positions of the cell tissue samples. A nitrogen laser was used as a radiation source. The electromagnetic radiation used for the inherent fluorescence excitation of the cell tissue had a wavelength of 337 nm.

The collected cell samples were cooled to a temperature of 15° C. and maintained at this temperature at least until after the end of the examination.

After the deactivation of the radiation source at $t_0$, the electromagnetic radiation emitted as a consequence of the inherent fluorescence of cell tissue was directed via the same optical fiber to a spectrometer with which a detection was possible in the wavelength interval from approximately 300 nm to approximately 600 nm.

A characteristic wavelength of 421 nm was selected at which the increased intensities of the inherent fluorescence occurred.

In the detection, a sampling rate of 50 ps was maintained and a detection of the intensity was performed from the time $t_0$ over a time of 10 ns. An evaluation in accordance with the equations (1) to (3) was performed using the measured intensity values and the difference autocorrelation function was determined, as shown in FIG. 3.

Since noise was recorded on the decay behavior of the intensity of an individual wavelength, the evaluation was repeated in an analog form with formed mean values. In this respect, intensity values were utilized within a wavelength interval of 421 nm±9.5 nm. The intensity decay behavior thus determined is reproduced in FIG. 2. The averaging in this respect took place from 60 wavelengths from this wavelength interval which each have a difference from one another of 0.315 nm.

As can be seen from the diagram shown in FIG. 3, the value of the fractal dimension $D_F$ can be determined using the determined difference autocorrelation function and the rise of a straight line with $(t-t_0)^{2H}$ and with knowledge of the exponent H.

The determined value $D_F$ can be compared with a threshold value specific to a tumor for the respective examined position of the respective cell tissue sample. This threshold value was between 1.31 and 1.32 for the prostate tumors examined. Depending on the difference of the determined values for $D_F$, not only exclusively a good-bad statement can be obtained. More differentiated cell tissue states such as benign prostate hyperplasia (BPH) or prostatic intraepithelial neoplasia (PIN), as a precursor to a prostate carcinoma, can also be distinguished.

If the determined value $D_F$ is, however, below the threshold value, it can be assumed that the examined cell tissue is healthy cell tissue free of tumor cells at the respective cell tissue sample at least at the location of the sample at which the examination was carried out.

The invention can, however, also be carried out at at least two wavelengths which can be detected using the spectrometer and which have a larger spacing from one another. The temporal intensity decay behavior can thus, for example, be carried out at the wavelengths 370 nm and 430 nm, optionally also with a described averaging.

The invention claimed is:

1. A method for recognizing tumorous living cell tissue, comprising the steps of
    emitting electromagnetic radiation in a locally defined manner onto cell tissue by a radiation source,
    deactivating the radiation source and, after deactivating the radiation source,
    measuring inherent fluorescence intensity of the cell tissue excited by the electromagnetic radiation with time and spectral resolution using known sampling rate(s) for at least one wavelength using a detector,
    determining difference autocorrelation function C(t) of the inherent fluorescence intensity using the measured inherent fluorescence intensity,
    calculating fractal dimension $D_F$ for the irradiated cell tissue as a proportionality between the determined difference autocorrelation function C(t) and an exponential function with a time as a base and an exponent comprising the fractal dimension $D_F$, and
    using the calculated fractal dimension $D_F$ for a classification with respect to a presence of a tumor in the irradiated cell tissue.

2. A method in accordance with claim 1, characterized in that monochromatic electromagnetic radiation is used for the inherent fluorescence excitation of the irradiated cell tissue.

3. A method in accordance with claim 1, characterized in that the measured intensity values are detected within an interval around a wavelength of the excited inherent fluorescence and the difference autocorrelation function of the intensity decay behavior C(t) of the mean values which were calculated from the fluorescence intensities simultaneously detected for the different wavelengths within the wavelength interval is determined and the fractal dimension $D_F$ for the irradiated cell tissue is calculated.

4. A method in accordance with claim 1, characterized in that detection is carried out at a constant sampling rate.

5. A method in accordance with claim 1, characterized in that the detection is carried out using a spectrometer and detection is performed at a sampling rate≤1000 ps.

6. A method in accordance with claim 1, characterized in that the irradiation and detection are carried out in an optically non-transparent chamber.

7. A method in accordance with claim 1, characterized in that monochromatic radiation having a wavelength of 337 nm is used for the excitation of the inherent fluorescence and the detection is carried out within a wavelength interval of 421.7 nm±15 nm.

8. A method in accordance with claim 1, characterized in that at least 30 wavelengths from the wavelength interval are considered for the averaging.

9. A method in accordance with claim 1, characterized in that the electromagnetic radiation for the excitation of the inherent fluorescence is directed to the cell tissue via at least one optical fiber and the inherent fluorescent light is directed to the detector via the same optical fiber(s) after the deactivation of the radiation source.

10. A method in accordance with claim 1, characterized in that the cell tissue sample to be detected is cooled before and during the detection and is maintained at a constant temperature in so doing.

11. A method in accordance with claim 1, characterized in that prostate cell tissue is used for a cell tissue sample.

12. A method in accordance with claim 1, characterized in that the classification is carried out with respect to a presence of a tumor by a comparison with a threshold value specific to a tumor.

13. A method in accordance with claim 1, characterized in that the classification with respect to the presence of a tumor takes place by an indication of a probability for a presence of a tumor.

14. A method for recognizing tumorous cell tissue at collected living cell tissue samples, comprising the steps of
emitting, using a radiation source, electromagnetic radiation in a locally defined manner onto a cell tissue sample,
deactivating the radiation source and, after deactivating the radiation source,
measuring inherent fluorescence intensity of the cell tissue excited by the electromagnetic radiation at the cell tissue with a detector in a time resolved and spectrally resolved manner at known sampling rate(s) for at least one wavelength,
determining difference autocorrelation function C(t) of the inherent fluorescence intensity using the measured inherent fluorescence intensity,
calculating fractal dimension $D_F$ for the irradiated cell tissue as a proportionality between the determined difference autocorrelation function C(t) and an exponential function with time as a base and an exponent comprising the fractal $D_F$ and
using the calculated fractal dimension $D_F$ for a classification with respect to a presence of a tumor in the respective irradiated cell tissue.

15. An apparatus, useful for carrying out the method in accordance with claim 1, comprising
a) a radiation source for directing electromagnetic radiation in a locally defined manner to cell tissue,
b) a detector for measuring inherent fluorescence intensity of the cell tissue in a time resolved and spectrally resolved manner, and connected to the detector
c) an electronic evaluation unit with which the difference autocorrelation function C(t) can be determined from the measured inherent fluorescence intensity, the fractal dimension $D_F$ can be calculated therefrom, and the calculated fractal dimension $D_F$ can be compared with a threshold fractal dimension typical for a tumor.

* * * * *